United States Patent
Mirabella

(10) Patent No.: US 6,625,252 B2
(45) Date of Patent: Sep. 23, 2003

(54) EMERGENCY VEHICLE WITH MEDICAL IMAGE SCANNER AND TELERADIOLOGY SYSTEM

(75) Inventor: Paul J. Mirabella, Brookfield, WI (US)

(73) Assignee: GE Medical Systems Global Technology Co., LLC, Waukesha, WI (US)

(*) Notice: Subject to any disclaimer, the term of this patent is extended or adjusted under 35 U.S.C. 154(b) by 0 days.

(21) Appl. No.: 10/225,654

(22) Filed: Aug. 22, 2002

(65) Prior Publication Data

US 2002/0191744 A1 Dec. 19, 2002

Related U.S. Application Data

(63) Continuation of application No. 09/628,656, filed on Jul. 28, 2000, now Pat. No. 6,481,887.
(60) Provisional application No. 60/196,354, filed on Apr. 12, 2000.

(51) Int. Cl.[7] .................................................. H05G 1/00
(52) U.S. Cl. ...................................... 378/102; 378/198
(58) Field of Search ........................ 296/24.1; 378/102, 378/198, 208, 209

(56) References Cited

U.S. PATENT DOCUMENTS

| | | | |
|---|---|---|---|
| 4,181,347 A | * | 1/1980 | Clark |
| 4,449,746 A | * | 5/1984 | Clark |
| 4,764,870 A | * | 8/1988 | Haskin |
| 5,097,497 A | * | 3/1992 | Deucher et al. |
| 5,619,763 A | * | 4/1997 | Randolph et al. |
| 5,727,353 A | * | 3/1998 | Getz et al. |
| 5,755,478 A | * | 5/1998 | Kamlya et al. |
| 5,775,758 A | * | 7/1998 | Eberspacher |
| 6,038,469 A | * | 3/2000 | Karlsson et al. |
| 6,082,799 A | * | 7/2000 | Marek |
| 6,179,358 B1 | * | 1/2001 | Hirayama et al. |

OTHER PUBLICATIONS

Press Release Sonera News, Sep. 8, 1997, Telecom Finland takes telemedicine mobile. www.sonera.fi/english/press/telemed.html.

Smith, DV, Smith, S; Bender, GN; Carter, JR; MDIS System at Madigan Army Medical Center, Jan. 25, 1995, Lessons learned and two years clinical experience in implementing the Medical Diagnostic Imaging Support (MDIS) System at Madigan Army Medical Center. www.matmo.org/pages/library/papers/mdispapers/spie94mamc.html.

(List continued on next page.)

Primary Examiner—David V. Bruce
(74) Attorney, Agent, or Firm—Ziolkowski Patent Solutions Group, LLC; Michael A. Della Penna; Carl B. Horton

(57) ABSTRACT

A mobile medical image scanner and teleradiology system are incorporated into an ambulance or other vehicle to permit a patient to be diagnosed while en route to a treatment facility such as a trauma center. The system obtains medical image data while the patient is being transported in the vehicle and transmits the medical image data to a receiver at a location which is remote from the vehicle. At the remote location, the transmitted medical image data is displayed in a humanly discernable manner and interpreted by a qualified physician, who then communicates diagnostic information to the technicians in the vehicle and/or to the treating physicians at the treatment facility. By providing diagnostic information back to the treating physicians prior to the patient's arrival at the treatment facility, the patient can be routed directly to the operating room, or the intensive care unit as necessary, thereby saving valuable time. The patient can even receive some care in the vehicle based on the diagnoses before he or she reaches the treatment facility. Patient survival rates are substantially improved due to the reduction in the diagnostic time required after the patient arrives at the trauma center.

24 Claims, 3 Drawing Sheets

OTHER PUBLICATIONS (*BW*)(*CA–Telenetics*)(*TLNT*) Feb. 29, 2000, Telenectics will demonstrate its airwave wireless technology at Industry Exhibit in Miami, www.businesswire.com/cgi–bin/f_headline.cgi?bw.022900/200601130&ticker=TLNT.

*ACR Standards*, Jan. 1, 1999, ACR Standard for Teleradiology.

Orphanoudakis, SC; IST '98, Vienna, Nov. 30–Dec. 2, 1998, *Healthcare Sector*, The wireless vision www.ics.forth.gr/ICS/acti/cmi_hta/publications/papers/1998/ist98/ist98.html.

*MIRG Research*, MOMEDA—Mobile Medical Data www.mirg.oulu.fi/Research/Teleradiology/.

*Virtual Hospital:Radiology:Nuclear Medicine: Teleradiology:Components*, 1992–1999 University of Iowa Hispitals and Clinics www.vh.org/Welcome/UIHC/UIHCMedDepts/DiagnosticRadiology/T . . . /components.htm.

*Sonera News*, Research Areas, Telemedical Solutions for the Health Care Sector "Move the information,k not the patient" www.sonera.fi/english/rd/telemed.html.

*Images–On–Call*, Teleradiology Networks www.imagesoncall.com/WhyImages–on–Call.html.

*Sonera News*, Telemedicine Status 1998 www.sonera.fi/english/rd/status.html.

Garshnek, V, Logan JK, Hassell, LH, *Quasar*, Feb. 16, 1998, Telemedicine defined, The telemedicine frontier: going the extra mile www.quasar.rog/21698/knowledge/telemedicine_frontier.html.

*Telesonography.com*, Interactive real–time ultrasound telediagnosis www.telesonography.com/TechnicalPrinter.html.

* cited by examiner

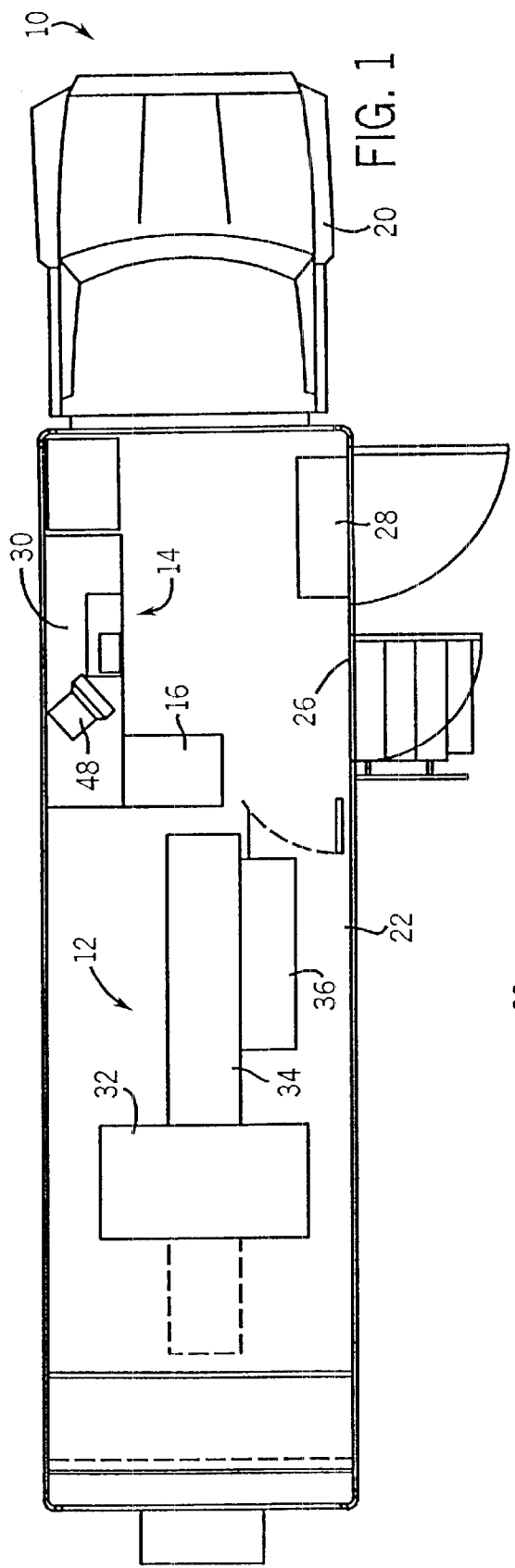
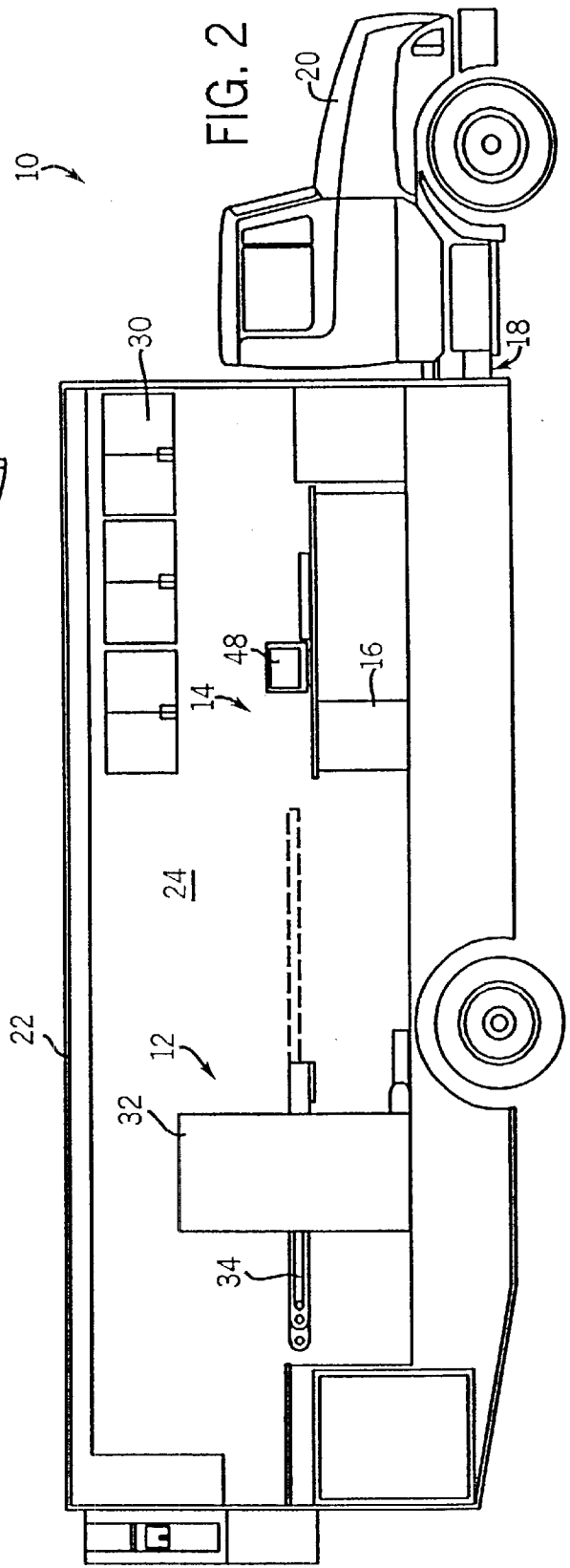

EMERGENCY VEHICLE WITH MEDICAL IMAGE SCANNER AND TELERADIOLOGY SYSTEM

CROSS REFERENCE TO RELATED APPLICATION

The present invention is a continuation and claims priority of U.S. Ser. No. 09/628,656 filed Jul. 28, 2000 entitled "Emergency Vehicle with Medical Image Scanner and Teleradiology System and Method of Operation", now U.S. Pat. No. 6,481,887, which claims priority of U.S. Ser. No. 60/196,354 filed Apr. 12, 2000.

FIELD OF THE INVENTION

The present invention relates generally to a specialized emergency vehicle having an on-board medical imaging scanner and teleradiology system and to a method of operation associated therewith.

BACKGROUND OF THE INVENTION

In most blunt and/or severe trauma cases, particularly those involving subdural hemotoma or internal bleeding, from, for example, auto accidents or a fall, the patient, is typically attended to in the first instance by emergency trauma technicians sent to the scene by an ambulance. Generally, these technicians obtain vital signs and statistics, stabilize the patient if possible, and transport the patient to an emergency room.

Once the patient arrives at the emergency room, if the blunt trauma and patient symptoms suggest any of the above conditions, the patient is then sent to the Radiology Department where, typically, a computed tomography (CT) scan is, in almost all cases, the diagnostic modality of choice. However, critical time passes during patient transport to the hospital. The chances of survival diminish in direct proportion to the amount of time that has passed since the initial trauma. That is, by the time the patient is transported to the hospital, a CT scan is performed, the images are read, and a diagnosis is made, the medical staff has lost critical time needed to save the patient. This is particularly problematic in rural areas where a patient may have to be transported many miles to the hospital.

Prior art CT scanner systems have been hardened and shock isolated to enable them to be used in various applications ranging from large mobile vans, trailers, relocatable vehicles, and, in the Gulf War, in transportable containers (such as iso-shelters) deployed by helicopter or truck. In this manner, CT scanners have been available as a diagnostic tool at various remote sites.

Various teleradiology systems are known. Teleradiology is the electronic transmission of radiological images from one location to another for the purposes of interpretation and/or consultation. For example, during the Gulf War, technicians or medics operated CT scanners in a remote location, and teleradiology systems were used to transmit the resulting images from the remote location to radiologists at a different location. In this manner, a second opinion could be obtained regarding the course of treatment for a patient.

However, due to limitations on the communication capabilities and on the ability to acquire images while the CT equipped vehicle is traveling, existing mobile teleradiology systems are incapable of acquiring CT images and transmitting those images to a treatment facility while the patient is en route to the treatment facility. In fact, the typical "mobile" CT vehicle is designed to be moved to a fixed site, such as a medical facility, used at that site, then moved to another fixed site for use at that site. Such transportable CTs are not designed to acquire images while in transit, and thus are ill-equipped to serve both as a mobile CT scanner and as an ambulance. Generally then, the need therefore continues to exist to provide a vehicle that is equipped to acquire medical images of a patient while in transit and to transmit those images to a remote location while the patient is en route to a treatment facility.

SUMMARY OF THE INVENTION

In accordance with one aspect of the invention, a specialized emergency vehicle, roughly the size of a large ambulance, is designed to contain all of the emergency and trauma equipment of a regular ambulance, but is also designed to contain a shock and vibration isolated medical scanner and a teleradiology system. The medical scanner is used to obtain medical images of a patient, and the teleradiology system operates to convert the medical images to transmittable medical image data and transmits the medical image data to a remote location while the vehicle is traveling.

The teleradiology system preferably includes a frame grabber coupled to the medical scanner and a digitizer coupled to the medical scanner and to the transmitter. It may additionally include a compressor which is coupled to the digitizer and to the transmitter and which is configured to compress digital data from the digitizer prior to transmission of the data by the transmitter.

In order to facilitate the transfer of a patient to and from the medical scanner, the vehicle may additionally include a patient support structure which is removably couplable to an imager tabletop and which serves as a mechanism for transferring a patient from a gurney to the imager tabletop.

In accordance with another aspect of the invention, a system is provided for remotely diagnosing a patient who is en route to a treatment facility. The system includes an emergency vehicle and a receiver and workstation located remote from the vehicle. The vehicle includes a mobile chassis, an enclosure which is disposed on the chassis and which forms a treatment/scanning bay, a medical image scanner which is located in the bay, the scanner being mounted on the chassis in a sufficiently hardened and shock isolated manner to permit medical image scans to be performed while the vehicle is traveling, and a teleradiology system which is located in the bay. The teleradiology system includes a computer which receives medical image data from the medical image scanner, and a transmitter which is coupled to the computer and which is configured to transmit medical image data while the vehicle is traveling. The remote receiver is configured to receive the transmitted medical image data. The workstation is coupled to the receiver and is configured to generate and display humanly discernable medical images from the data. The workstation preferably is configured to convert the received medical image data into a visually displayed modified medical image. It may be located either at the same facility as a treatment facility serving as a destination for the vehicle, or at a different facility.

In accordance, with still another aspect of the invention, a method is provided of remotely diagnosing a patient who is en route to a treatment facility such as a trauma center. The method includes obtaining medical image data from a patient in an ambulance or similar vehicle while the vehicle is en route to a treatment facility; transmitting the medical image data to a receiver at a location which is remote from the vehicle, and receiving the medical image data at the receiver. At the remote location, the transmitted medical image data is displayed in a humanly discernable manner and interpreted by a qualified physician, who then communicates diagnostic information either to the technicians in the vehicle or to the treating physicians at the trauma center. By providing diagnostic information to the treating physicians prior to the patient's arrival at the trauma center, the patient can be routed directly to the operating room, or the intensive care unit as necessary, thereby saving valuable time. The patient can even receive some care in the vehicle based on the diagnoses before he or she reaches the treatment facility.

An important benefit of the invention is an improved patient survival rate due to the reduction in the diagnostic time required after the patient arrives at the trauma center. This invention allows critical patient data to be delivered to the relevantly trained physicians faster and more efficiently especially in life-threatening situations.

Various other features, objects and advantages of the invention will be made apparent to those of ordinary skill in the art upon review of the following detailed description and drawings.

BRIEF DESCRIPTION OF THE DRAWINGS

The drawings illustrate the best mode presently contemplated for carrying out the invention FIG. 1 is a top view of an emergency vehicle having a medical image scanner mounted therein in accordance with the present invention;

FIG. 2 is a side view of the emergency vehicle shown in FIG. 1;

DETAILED DESCRIPTION OF THE PREFERRED EMBODIMENT

Figure 3:
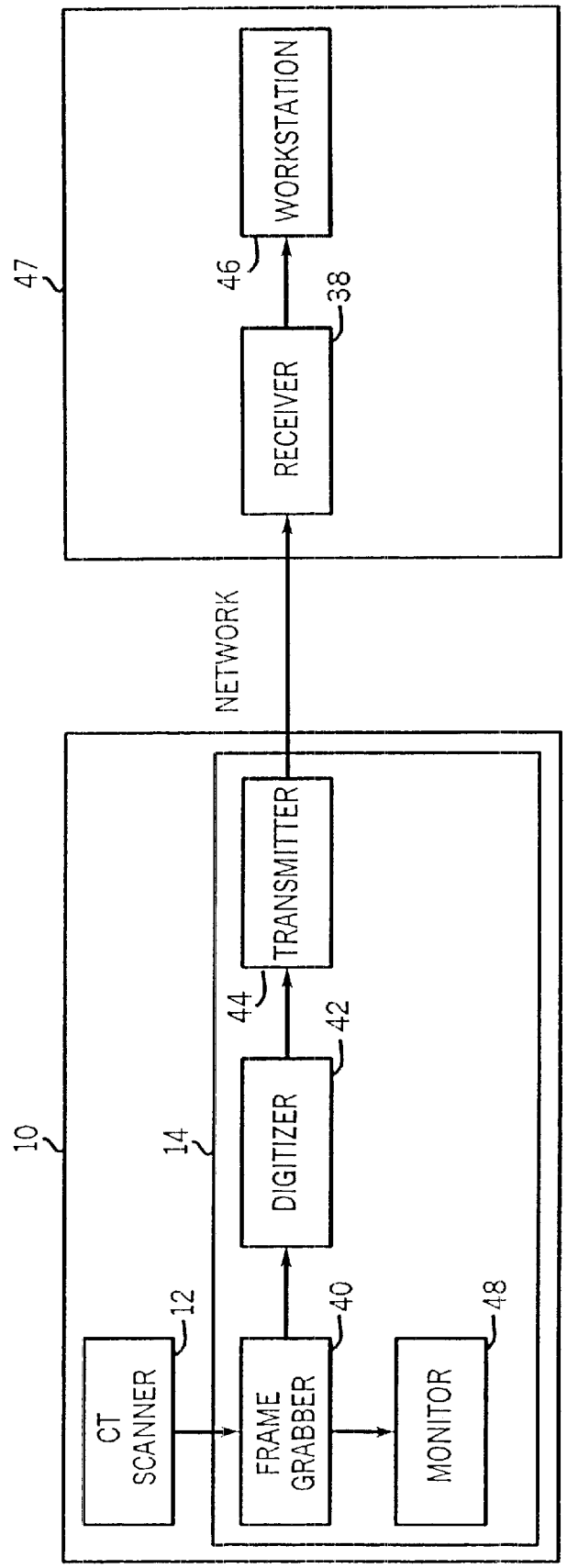
FIG. 3 is a schematic diagram of the teleradiology system of the vehicle of FIGS. 1 and 2.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIGS. 1 and 2 illustrate an emergency vehicle 10 having a diagnostic medical image scanner 12, such as MRI, x-ray, CT, or any other diagnostic imaging device. In a preferred embodiment the medical image scanner is a CT imager and the vehicle 10 includes a teleradiology system 14 contained therein. The medical image scanner 12 and teleradiology system 14 are controlled by an operator stationed at a console 16. The vehicle 10 may be configured as a van, an ambulance, or any other vehicle large enough to accommodate the medical image scanner 12, the teleradiology system 14, and related emergency equipment, yet small enough to navigate most streets and roads. The dimensions of the vehicle 10 in the preferred embodiment are approximately 40 feet (12.2 m) in length, 102 inches (2.9 m) wide, and 12 feet 10 inches (3.9 m) in height. The vehicle 10 includes a mobile chassis 18 supporting a front operator's cab 20 and a rear enclosure 22 that encloses a scanning/treatment bay 24. An entrance/exit 26 and a wheelchair lift 28 are provided for transporting patients into and out of the bay 24 of the vehicle 10. Optionally, a patient bed lift (not shown) can be installed with an entry directly to the area of the medical image scanner 12. Standard emergency/trauma treatment equipment is also located in the bay 24 and stored in cabinets 30. This equipment may comprise medical instruments, dressings, drugs, a defibrillator, etc.

In the preferred embodiment, a small foot-print, slip ring technology, rapid scan CT scanner (for example, a CT/e from General Electric Medical Systems) is utilized as the medical image scanner 12. The CT scanner 12 is isolated from shock and vibration so that it can be operated as the vehicle 10 is en route to a trauma center or other treatment facility. The CT scanner 12 includes a scanning device 32 and a patient table 34 that is horizontally reciprocatable through the scanning device 32 in a conventional manner. Vehicles incorporating shock and vibration isolation measures suitable to permit scanning within them are known and disclosed, for example, in U.S. Pat. Nos. 4,181,347 and 4,449,746.

The medical image scanner 12 of the present invention optionally includes a patient-handling system or a patient table that would include a removable, detachable patient support structure 36 including a tabletop or cradle. Support structure 36 can also be used in place of the canvas or polymer mobile table (gurney) used to transport the patient from the accident site to the vehicle 10. The support structure 36 would work as a normal gurney in all other ways. The patient can be wheeled on this gurney to the vehicle 10. As the gurney is slid into the vehicle 10, the cradle or tabletop forming the support structure 36 would "dock" with the receiving patient table 34. As soon as the support structure 36 is locked in place, the gurney could be removed and stowed. Alternatively, a standard gurney could be used, and the patient could simply be lifted onto the tabletop 34.

Figure 4:
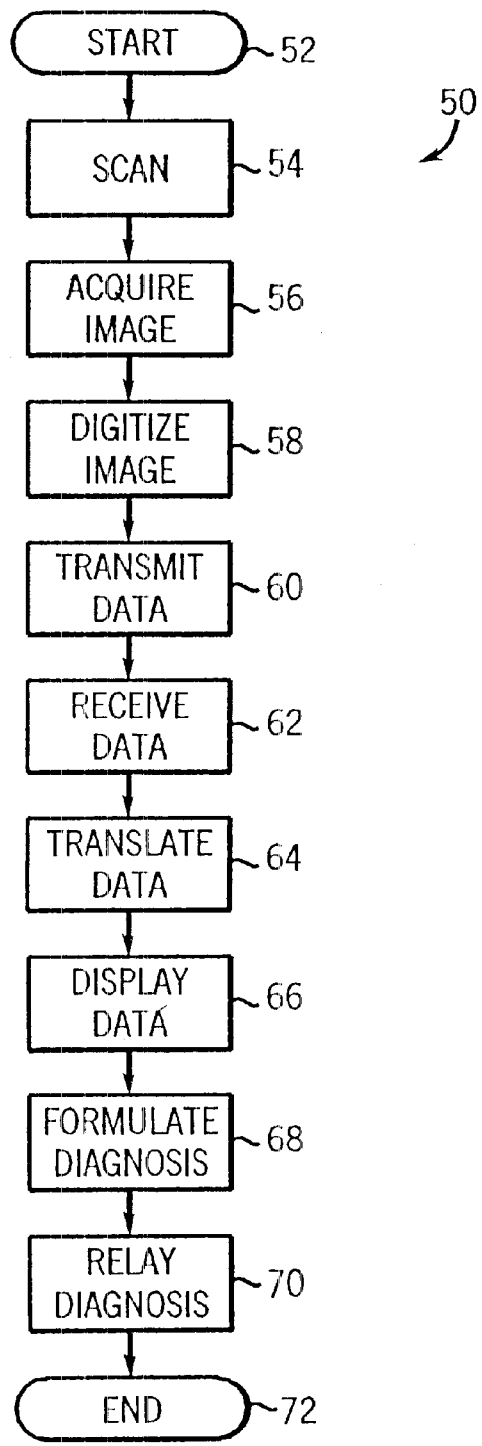
FIG. 4 is a flowchart of a telediagnostic procedure performable in accordance with the present invention.

Referring to FIG. 3, the teleradiology system 14 interfaces with the medical image scanner 12 and with a remote receiver 38. The teleradiology system 14 includes a frame grabber 40, a monitor 48, a digitizer 42, and a wireless transmitter 44. Wireless transmitter 44 is configured to transmit signals to (and possibly also receive signals from) the remote receiver 38. The receiver 38 (which may also be capable of transmission) is coupled to a remote workstation 46 located at a trauma center 47 or other facility staffed by a radiologist or other diagnostician. Images produced by the teleradiology system 14 may also be displayed by a monitor 48 located on-board the vehicle 10 (FIGS. 1 and 2). The operation of the vehicle 10 will now be described with reference to the flowchart of FIG. 4. The routine 50 of this flowchart proceeds from START at 52 after the patient is placed on the patient table 34. The patient (or the relevant portions of the patient such as the head, chest, and/or abdomen) is scanned using the medical image scanner 12 at 54 as the vehicle 10 is en route to the treatment facility. The scanned image is acquired at 56 using the frame grabber 40 and, if desired, displayed on the monitor 48. The acquired image is digitized at 58 to produce a transmittable medical image data. This data may, if desired, be compressed using a digital compressor (not shown) to facilitate transmission and storage of the medical image data.

The medical image data is then transmitted, via the wireless transmitter 36, to the remote receiver 38 at 60. Transmission may be by way of any IR, microwave, or other wireless signal capable of reliably and rapidly transmitting relatively large quantities of digitized data from a moving vehicle to a selected location or to a selected number of desired locations. Transmission preferably takes place in asynchronous mode over a networked broadband wireless network such as a networked Wireless Local Area Network (WLAN), a networked High Performance Radio Local Area Network (HIPERLAN), or a Wireless Wide Area Network (WWAN).

At step 62, the medical image data is received by the receiver 38 and is then translated to a modified medical image at 64. The modified image is then displayed at the workstation 46 at 66 and viewed by a radiologist or other trained professional.

The radiologist or other trained professional then interprets the modified medical image at the display workstation 46, formulates a diagnosis at 68, and communicates his or her recommendations to the emergency room physicians or back to the technicians in the vehicle 10 at 70. The routine 50 then proceeds to END at 72. In this manner, image acquisition, transmission, and evaluation have been performed in whole or in part when the patient arrives at the trauma center or other treatment facility, and the patient, upon receipt, can be immediately triaged to the appropriate department (operating room, intensive care, etc.), thereby saving valuable time. In addition, if the diagnosis is made while the vehicle is still en route to the treatment facility, the diagnosis can then be relayed back to personnel in the vehicle 10, who may then initiate a treatment protocol based on the diagnosis.

It is important to note that that the receiver 38 and workstation 46 need not be at the same location as the treatment facility. For instance, a patient could be scanned while the vehicle 10 is en route to a first location, and the image could be transmitted to a radiologist at a second, more remote location, who would then make a diagnosis and relay it to the personnel in the vehicle 10 and/or at the first location. Images could also be transmitted simultaneously or in sequence to multiple receivers at multiple locations, thereby facilitating second opinions.

It is understood that the invention is not confined to the particular construction and arrangement of parts herein illustrated and described, but embraces all such modified forms thereof as may come within the scope of the following claims. It will be apparent that many modifications and variations are possible in light of the above teachings. For example, although the preferred embodiment utilizes a CT scanner, the invention is well suited for use with other imaging devices as is evident to those skilled in the art.

It therefore is to be understood that within the scope of the appended claims, the invention may be practiced other than is specifically described. Alternative embodiments and variations of the method taught in the present specification may suggest themselves to those skilled in the art upon reading of the above description. Various other features and advantages of the invention are set forth in the following claims.

What is claimed is:

1. An emergency vehicle comprising:
   (A) a mobile chassis;
   (B) an enclosure which is disposed on the chassis and which forms a treatment/scanning bay;
   (C) emergency and/or trauma equipment which is located in the treatment/scanning bay;
   (D) a medical image scanner which is located in the treatment/scanning bay, the medical image scanner being mounted on the mobile chassis in a sufficiently hardened and shock isolated manner to permit medical image scans to be performed while the emergency vehicle is traveling; and
   (E) a teleradiology system which is located in the treatment/scanning bay and which includes
      (1) a computer which receives medical image data from the medical image scanner, and
      (2) a transmitter which is coupled to the computer and which is configured to transmit medical image data to a remote receiver while the vehicle is traveling.

2. The emergency vehicle of claim 1 wherein the computer includes a frame grabber coupled to the medical image scanner and a digitizer coupled to the medical image scanner and to the transmitter.

3. The emergency vehicle of claim 2 further comprising a digital compressor coupled to the digitizer and to the transmitter and configured to compress digital data from the digitizer prior to transmission of the medical image data by the transmitter.

4. The emergency vehicle of claim 1 wherein the medical image scanner is a CT scanner and further includes a patient table, and a patient support structure which is removably couplable to the patient table and which serves as a mechanism for transferring a patient from a gurney to the patient table.

5. In combination:
   (A) an emergency vehicle including
      (1) a mobile chassis;
      (2) an enclosure which is disposed on the mobile chassis and which forms a treatment/scanning bay;
      (3) a medical image scanner which is located in the treatment/scanning bay, the medical image scanner being mounted on the mobile chassis in a sufficiently hardened and shock isolated manner to permit medical image scans to be performed while the vehicle is traveling, and
      (4) a teleradiology system which is located in the treatment/scanning bay and which includes
         (a) a computer which receives medical image data from the medical image scanner, and
         (b) a transmitter which is coupled to the computer and which is configured to transmit medical image image data while the vehicle is traveling;
   (B) a receiver located remotely from the emergency vehicle and configured to receive the transmitted medical image data; and
   (C) a workstation located remotely from the emergency vehicle and coupled to the receiver, and which is configured to generate and display humanly discernable medical images of the transmitted medical image data.

6. The combination of claim 5 wherein the medical image scanner is a CT scanner and computer includes a frame grabber coupled to the CT scanner and a digitizer coupled to the CT scanner and to the transmitter.

7. The combination of claim 6 wherein the workstation is configured to convert the received medical image data into a visually displayed modified CT image.

8. The combination of claim 5 wherein the workstation is located in the same facility as a treatment facility serving as a destination for the emergency vehicle.

9. The combination of claim 5 wherein the workstation is located in a different facility as a treatment facility serving as a destination for the emergency vehicle.

10. The combination of claim 5 further comprising emergency and/or trauma equipment which is located in the treatment/scanning bay of the emergency vehicle.

11. An emergency vehicle comprising:
    (A) a mobile chassis having an operator cab area mounted thereon;

(B) an enclosure which is disposed on the chassis and which forms a treatment/scanning bay;

(C) emergency and/or trauma equipment which is located in the treatment/scanning bay;

(D) a medical image scanner which is located in the treatment/scanning bay, the medical image scanner being mounted on the mobile chassis in a sufficiently hardened and shock isolated manner to permit medical image scans to be performed while the emergency vehicle is traveling; and (E) a teleradiology system which is located in the treatment/scanning bay and which includes
  (1) a computer which receives medical image data from the medical image scanner, and
  (2) a transmitter which is coupled to the computer and which is configured to transmit medical image data to a remote receiver while the vehicle is traveling.

12. The emergency vehicle of claim 11 further comprising a wheelchair lift configured to transport patients into and out of the treatment/scanning bay.

13. The emergency vehicle of claim 11 incorporated as one of a van and an ambulance.

14. The emergency vehicle of claim 11 wherein the computer includes a frame grabber coupled to the medical image scanner and a digitizer coupled to the medical image scanner and to the transmitter.

15. The emergency vehicle of claim 14 comprising a digital compressor coupled to the digitizer and to the transmitter and configured to compress digital data from the digitizer prior to transmission of the medical image data by the transmitter.

16. The emergency vehicle of claim 11 wherein the medical image scanner is a CT scanner and further includes a patient table, and a patient support structure which is removably couplable to the patient table and which serves as a mechanism for transferring a patient from a gurney to the patient table.

17. The emergency vehicle of claim 11 being approximately 40 feet in length, 102 inches wide, and 12 feet 10 inches in height.

18. In combination:
(A) an emergency vehicle including
  (1) a mobile chassis;
  (2) an enclosure which is disposed on the mobile chassis and which forms a treatment/scanning bay;
  (3) an operator cab permanently connected to the enclosure;
  (4) a medical image scanner which is located in the treatment/scanning bay, the medical image scanner being mounted on the mobile chassis in a sufficiently hardened and shock isolated manner to permit medical image scans to be performed while the vehicle is traveling, and
  (5) a teleradiology system which is located in the treatment/scanning bay and which includes
    (a) a computer which receives medical image data from the medical image scanner, and
    (b) a transmitter which is coupled to the computer and which is configured to transmit medical image image data while the vehicle is traveling;
(B) a receiver located remotely from the emergency vehicle and configured to receive the transmitted medical image data; and
(C) a workstation located remotely from the emergency vehicle and coupled to the receiver, and which is configured to generate and display humanly discernable medical images of the transmitted medical image data.

19. The combination of claim 18 wherein the workstation is configured to convert the received medical image data into a visually displayed modified CT image.

20. The combination of claim 18 wherein the workstation is located in the same facility as a treatment facility serving as a destination for the emergency vehicle.

21. The combination of claim 18 wherein the emergency vehicle is incorporated into a van having no more than three axles.

22. An ambulatory vehicle comprising:
(A) a self-powered mobile chassis operable as an emergency vehicle to transport and treat patients in need of medical treatment;
(B) an enclosure which is disposed on the chassis and which forms a treatment/scanning bay;
(C) emergency and/or trauma equipment which is located in the treatment/scanning bay; and
(D) a medical image scanner which is located in the treatment/scanning bay, the medical image scanner being mounted on the mobile chassis in a sufficiently hardened and shock isolated manner to permit medical image scans to be performed while the emergency vehicle is traveling.

23. The emergency vehicle of claim 22 wherein the chassis includes no more than three axles.

24. The emergency vehicle of claim 23 wherein the chassis includes no more than two axles.

* * * * *